United States Patent [19]

Burley

[11] 4,305,883

[45] Dec. 15, 1981

[54] PROCESS FOR THE PREPARATION OF BIS-(CYANOETHYL) TIN DIHALIDES

[75] Inventor: Joseph W. Burley, St. Helens, Great Britain

[73] Assignee: Akzo N.V., Ijssellaan, Netherlands

[21] Appl. No.: 125,698

[22] Filed: Feb. 28, 1980

[30] Foreign Application Priority Data

Feb. 28, 1979 [GB] United Kingdom .............. 07096/79

[51] Int. Cl.$^3$ .............................................. C07F 7/22
[52] U.S. Cl. ................................................. 260/429.7
[58] Field of Search ..................................... 260/429.7

[56] References Cited

U.S. PATENT DOCUMENTS

| | | | |
|---|---|---|---|
| 3,440,255 | 4/1969 | Matsuda et al. ................ | 260/429.7 |
| 3,607,893 | 9/1971 | Reifenberg ...................... | 260/429.7 |
| 4,080,363 | 3/1978 | Hutton et al. ................... | 260/429.7 |
| 4,196,137 | 4/1980 | Wirth et al. ..................... | 260/429.7 |

*Primary Examiner*—Helen M. S. Sneed
*Attorney, Agent, or Firm*—Stevens, Davis, Miller & Mosher

[57] ABSTRACT

In the process of this invention bis-(cyanoethyl) tin dihalides are prepared by reacting metallic tin with acrylonitrile and hydrogen halide in an inert solvent.

3 Claims, No Drawings

PROCESS FOR THE PREPARATION OF BIS-(CYANOETHYL) TIN DIHALIDES

The present invention relates to a process for the preparation of bis-(cyanoethyl) tin dihalides of general formula:

$$X_2Sn(CH_2-CH_2-CN)_2 \qquad (I)$$

wherein X is either Cl or Br.

The organotin halides of formula I are known in the art. They can be prepared by various methods, such as by electrolysis and subsequent disproportionation (J. Organometal. Chem., 10 (1967) 285–289) and by a hydrostannation route (J. Organometal. Chem., 9 (1967) 505–509). A method involving a direct reaction between metallic tin and a cyanoethyl halide is disclosed in U.S. Pat. No. 3,440,255.

Generally for reasons such as expensive starting materials, cumbersome reaction conditions, low product yield or difficult isolation, these known methods are not acceptable for commercial application.

It is, nevertheless useful to have a commercially viable method available because these compounds have particular utility as intermediates in the manufacture of organotin stabilizers for polyvinylchloride and related polymers.

Accordingly, the present invention provides a method for the preparation of bis-(cyanoethyl) tin dihalide of the general formula

$$X_2Sn(CH_2-CH_2-CN)_2 \qquad (I)$$

wherein X is either Cl or Br, which method comprises reacting in an inert solvent medium metallic tin with acrylonitrile and either hydrogenchloride or hydrogen bromide and recovering the organotin dihalide. The method of the present invention is straightforward, employs readily available and relatively inexpensive starting meterials, while reaction and product isolation proceed smoothly under moderate conditions.

Temperature appears to have some effect on the preparation in that the desired reaction occurs in preference to side reactions, such as the hydrochlorination of the cyano group, at temperature above ambient temperature. Preferably the reaction is carried out at a temperature above about 40° C.

It is essential that the solvent medium be inert with respect to the cyano group in order to avoid hydrolysis, or similar conversion, of this group. Such inert solvents can generally be found among the aliphatic and aromatic hydrocarbons, chlorinated hydrocarbons, ketones and ethers. Very useful solvents are to be found in the class of aliphatic and cyclic ethers. Preferred species of that class are dimethoxyethane and tetrahydrofuran.

With regards to this solvent aspect, the method of this invention essentially differs from the method disclosed in German Pat. Publication No. 2,819,536. In the method described in this publication the reaction is carried out in the presence of either water, alcohol or carboxylic acid so as to convert in-situ the cyano group to a carbonyl containing group.

As mentioned above the bis-(cyanoethyl) tin dihalides are useful intermediates in the preparation of PVC stabilizers. Thus, the cyanoethyltin thioglycollates and carboxylates are effective stabilizers compared to the conventional butyl tin analogues, particularly in the area of emulsion resins. They also show a marked synergism with epoxy compounds when these are included in the resin formulation.

Further to illustrate this invention specific examples are described below.

EXAMPLE 1

134.1 g acrylonitrile, 150 ml dimethoxyethane and 150 g powdered tin was charged to a 500 ml three neck round bottom flask equipped with heating mantle, stirrer, thermometer ans gas introduction tube. The temperature was raised to 60° C. and 113 g hydrogenchloride was added, with stirring, over a period of 21 hours.

A white solid precipitated from the solution as the reaction proceeded.

Filtration yielded 201.3 g of solid of which 11.4 was unreacted tin. The organotin compound was separated from the unreacted tin by solvent extraction with tetrahydrofuran and was characterized by spectroscopic techniques (I.R. and N.M.R.) and elemental analysis (Cl and Sn) to be $Cl_2Sn(CH_2CH_2CN)_2$. The yield was 189.9 g (55%).

EXAMPLE 11

100 g powdered tin was suspended in 89.4 g acrylonitrile and 300 ml dimethoxyethane using a flask similar to that used in the previous example. The temperature was raised to 40° C. and 178 g hydrogen bromide was passed through the mixture with stirring over 16½ hours.

The solvent was then removed under reduced pressure and 300 ml isopropyl acetate was added. The mixture was filtered to remove stannous bromide and the filtrate was evaporated. The residue was treated with further isopropyl acetate and refiltered.

The filtrate was evaporated to give 196.4 g of a reddish product (60% yield). I.R. and N.M.R. spectroscopy and elemental analysis indicated that the product was largely $Br_2Sn(CH_2CH_2CN)_2$.

I claim:

1. Process for preparing an organotin dihalide of the general formula

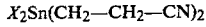

$$X_2Sn(CH_2-CH_2-CN)_2$$

wherein X is either chlorine or bromine, which comprises reacting in an inert solvent medium metallic tin with acrylonitrile and either hydrogen chloride or hydrogen bromide in the absence of other reactive compounds, and recovering said organotin dihalide.

2. Process according to claim 1 wherein the reaction is carried out at a temperature above about 40° C.

3. Process according to claim 1 wherein the reaction is carried out in an aliphatic or cyclic ether as the solvent medium.

* * * * *